US010662141B2

(12) United States Patent
Lange De Oliveira et al.

(10) Patent No.: US 10,662,141 B2
(45) Date of Patent: May 26, 2020

(54) PROCESS FOR HYDROGENATING TOLUENEDIAMINE (TDA) TAR

(71) Applicant: BASF SE, Ludwigshafen am Rhein (DE)

(72) Inventors: Armin Lange De Oliveira, Heidelberg (DE); Ines Lottenburger, Ludwigshafen (DE); Christian Bechtold, Ludwigshafen (DE); Thomas Heidemann, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/340,478

(22) PCT Filed: Oct. 9, 2017

(86) PCT No.: PCT/EP2017/075601
§ 371 (c)(1),
(2) Date: Apr. 9, 2019

(87) PCT Pub. No.: WO2018/069209
PCT Pub. Date: Apr. 19, 2018

(65) Prior Publication Data
US 2019/0241501 A1 Aug. 8, 2019

(30) Foreign Application Priority Data

Oct. 10, 2016 (EP) ..................................... 16193108

(51) Int. Cl.
*C07C 209/72* (2006.01)
*C07C 211/36* (2006.01)
*C07C 209/84* (2006.01)
*C07C 209/86* (2006.01)

(52) U.S. Cl.
CPC .......... *C07C 209/72* (2013.01); *C07C 211/36* (2013.01); *C07C 209/84* (2013.01); *C07C 209/86* (2013.01); *C07C 2601/14* (2017.05)

(58) Field of Classification Search
USPC ........................................................ 546/461
See application file for complete search history.

(56) References Cited

U.S. PATENT DOCUMENTS

| 5,728,880 A | 3/1998 | Beckhaus et al. |
| 5,773,657 A * | 6/1998 | Rutter ..................... B01J 21/04 502/313 |
| 5,936,126 A | 8/1999 | Ruehl et al. |
| 2006/0089507 A1 | 4/2006 | Sohn et al. |
| 2007/0083065 A1 | 4/2007 | Knoesche et al. |
| 2011/0251425 A1 | 10/2011 | Penzel et al. |
| 2011/0295039 A1 | 12/2011 | Raichle et al. |
| 2012/0289746 A1 | 11/2012 | Penzel et al. |
| 2013/0211141 A1 | 8/2013 | Raichle et al. |
| 2015/0218082 A1 | 8/2015 | Mueller et al. |
| 2016/0304436 A1 | 10/2016 | Schaack et al. |

FOREIGN PATENT DOCUMENTS

| CN | 101875614 A * | 11/2010 |
| EP | 1 106 600 A2 | 6/2001 |
| EP | 2 883 864 A1 | 6/2015 |
| WO | WO 00/35852 A1 | 6/2000 |
| WO | WO 2015/086638 A1 | 6/2015 |

OTHER PUBLICATIONS

Machine translation EP 2883864.*
Machine translation CN 101875614.*
International Search Report dated Nov. 3, 2017, in PCT/EP2017/075601 filed Oct. 9, 2017.

* cited by examiner

*Primary Examiner* — Ana Z Muresan
(74) *Attorney, Agent, or Firm* — Oblon, McClelland, Maier & Neustadt, L.L.P.

(57) ABSTRACT

Process for hydrogenating toluenediamine (TDA) tar containing TDA and high boilers relative to TDA, including the step of contacting the toluenediamine tar with a heterogeneous hydrogenation catalyst comprising at least one metal selected from the group consisting of Ni, Co, Ru, Pd, Pt on at least one catalyst support selected from the group consisting of carbon, $TiO_2$ and $ZrO_2$, and with hydrogen under hydrogenating conditions.

14 Claims, No Drawings

PROCESS FOR HYDROGENATING TOLUENEDIAMINE (TDA) TAR

This application is a National Phase of PCT/EP2017/075601, which was filed on Oct. 9, 2017. This application is based upon and claims the benefit of priority to European Application No. 16193108.4, which was filed on Oct. 10, 2016.

The present invention relates to a process for hydrogenating toluenediamine (TDA) tar containing TDA and high boilers relative to TDA and to the use of a specific heterogeneous hydrogenation catalyst therefore.

Toluenediamine, hereinafter referred to as TDA, is an aromatic amine which is frequently used in industry; it is, in particular, processed further to give tolylene diisocyanate which is predominantly used in polyurethane production. TDA is prepared industrially by catalytic hydrogenation of dinitrotoluene, hereinafter referred to as DNT.

Many catalysts have been developed for the above reaction in order to achieve a very high yield and selectivity in the reaction and also to discover catalysts which are stable at relatively high reaction temperatures.

The hydrogenation of DNT is strongly exothermic. It has therefore always been an aim to utilize the heat of reaction, for example in the form of steam.

As a reactor which is particularly suitable for removing the heat of reaction, WO 00/35852 A1 has proposed a reactor which has internal and external loop motion and is configured as a vertically upright apparatus having a driving jet nozzle at its upper end, via which the reaction mixture taken off from the reaction bottoms is injected via an exothermic loop into the upper region of the reactor and subsequently flows into a central plug-in tube which is arranged in the longitudinal direction of the reactor, flows through this tube from the top downwards, is there deflected by an impingement plate and again flows upward in an internal loop motion outside the plug-in tube. To remove the heat of reaction, heat exchangers, in particular field tubes, i.e. double tubes which are arranged vertically in the longitudinal direction of the reactor and in which the inner tube is open at the lower end to the outer tube and the outer tube is closed off at the bottom from the reaction space and in which a heat transfer medium, in particular water, flows and removes the heat of reaction, are provided in the interior of the reactor. In addition to the removal of heat via heat exchangers arranged in the interior of the reactor, a heat exchanger can also be provided in the external loop flow. In the process described in WO 00/35852 A1, aromatic amines are said to be produced in a high space-time yield and with significant suppression of secondary reactions.

In the prior art processes for purifying toluylenediamine (TDA) by distillation, the crude TDA obtained in the hydrogenation of dinitrotoluene is initially fed to a rectification column. In the rectification column, the low-boiling constituents are removed overhead. Low-boiling constituents are, for example, 3,4-TDA, ortho-toluidine and water. Ortho-toluidine and water occur merely in traces. The bottoms mixture obtained in the rectification comprises in particular 2,4-TDA, 2,6-TDA and an oligomer mixture which is formed from the TDA isomers present in the bottoms mixture. To remove the product of value comprising 2,4-TDA and 2,6-TDA, the bottoms mixture is fed to a thin-film evaporator. In the thin-film evaporator, the tolyene isomer mixture is removed. Such a process is described, for example, in SRI report 1A, 1968, page 55 to 65.

A further known means of removing the TDA isomer mixture from the bottoms mixture is the use of a second rectification column. Here, the TDA isomer mixture is drawn off over-head. The remaining bottoms which comprise in particular the oligomer mixture formed from the TDA isomers and the catalyst from the hydrogenation are fed to a suitable disposal operation.

A further method for the distillative recovery of toluylenediamine is disclosed in US 2007/0083065. For distillatively preparing TDA from a reactant stream comprising TDA, high boilers and low boilers, the separation is performed in a dividing wall column in which a dividing wall is disposed in the longitudinal direction of the column to form an upper combined column region, a lower combined column region, a feed section having a rectifying section and stripping section and also a withdrawal section having a rectifying section and stripping section.

TDA tar, which is the high-boiler fraction resultant from the DNT hydrogenation followed by distillative separation of low boilers and TDA, is an unwanted side-product of TDA and is currently incinerated at great cost. TDA tar typically contains significant amounts of TDA, typically in the range of 5 to 10 wt % with vicinal TDA percentage of 10 to 20% in order to keep it pumpable or flowable.

The disposal or incineration of significant amounts of TDA tar leads to a waste of the desired product TDA which is contained in the TDA tar and furthermore is not environmentally friendly and furthermore costly.

The object underlying the invention is to provide an alternative use for TDA tars which allows the yielding of desired products from the TDA tar, thus reducing the amount of non-useable TDA tar which has to be disposed of or incinerated.

The object is achieved by a process for hydrogenating toluenediamine (TDA) tar containing TDA and high boilers relative to TDA, including the step of contacting the toluenediamine tar with a heterogeneous hydrogenation catalyst comprising at least one metal selected from the group consisting of Ni, Co, Ru, Pd, Pt on at least one catalyst support selected from the group consisting of carbon, $TiO_2$ and $ZrO_2$, and with hydrogen under hydrogenating conditions.

The object is furthermore achieved by the use of the respective catalyst for hydrogenating toluenediamine (TDA) tar containing TDA and high boilers relative to TDA.

It has been found according to the present invention that by employing specific catalysts, the TDA tars can be hydrogenated to form value products such as methylcyclohexylamines (MCA) or methylcyclohexyldiamines (MCDA) or other suitable side products which typically are mid-boiler fractions or core-hydrogenated dimers of TDA. The latter can substitute TDA as a diluent so that TDA can be removed from the TDA tars without impairing its flow behavior or viscosity.

Alternatively, the above-mentioned value products can be isolated from the hydrogenated TDA tar without substituting TDA as diluent. This helps to avoid affecting the TDA-work-up. Mid-boilers such as core-hydrogenated dimers of TDA can also contain additional value products.

The value products are produced without feedstock costs, and incineration costs can be saved. In addition, catalyst residues in the TDA tar, typically nickel and $ZrO_2$ from the nitrotoluene (DNT) hydrogenation, can be isolated from the product by e.g. filtration.

In the process according to the present invention, the TDA tars can be used per se or can be diluted with an organic solvent or diluent inert to the hydrogenation before performing the hydrogenation.

It is furthermore possible to dilute the TDA tar with the products in recycle mode, i.e. with products which will be recycled into the TDA tar hydrogenation.

TDA tar is typically available from tolylene diisocyanate (TDI) production plants.

Typical processes for preparing aromatic amines like toluene diamine (TDA) are disclosed in US 2013/0211141, US 2007/0083065, and US 2011/0295039.

Processes for preparing aromatic isocyanates are for example disclosed in US 2011/0251425 and US 2012/0289746 as well as US 2006/0089507.

The process for the liquid-phase hydrogenation of dinitrotoluene by means of hydrogen in the presence of a suspended, often nickel-comprising catalyst is discussed in detail in US 2013/0211141. While this reference specifically refers to monitoring the amount of hydrogen and stopping the introduction of nitroaromatic compounds in order to avoid damage to the catalyst, the hydrogenation of dinitrotoluene to toluenediamine is broadly described. Reference can be made specifically to paragraphs [0048] to [0100]. Dinitrotoluene isomers are depicted in paragraph [0069]. The corresponding toluenediamines are depicted in paragraph [0071]. The process is discussed in detail in paragraphs [0089] to [0100]. Catalysts which can be employed for this hydrogenation of dinitrotoluene to toluenediamines are disclosed in paragraphs [0059] to [0065].

Typically, a loop reactor is employed in which the driving jet of an external circuit brings about circulating flow in the interior of the reactor. A central plug-in tube is arranged in the longitudinal direction of the reactor, a laminar or turbulent nitroaromatic jet from one or more of the feed devices for the nitroaromatic impinges in the process onto the surface of the liquid phase in the region of the cross-sectional area of the plug-in tube projected onto the liquid surface, see paragraphs [0097] to [0100].

To be able to drive the external circuit, a pump which can transport not only liquid but also gas and suspended solid is installed, see paragraph [0108]. The process is furthermore illustrated along the functional principle as described in WO 2000/35852, see above, in the examples of US 2013/0211141.

In the process, an amount of hydrogenation product is continuously taken off from the external product circuit on the pressure side of the second centrifugal pump and fed into a laminar clarifier. The catalyst is able to concentrate in the lower region of this clarifier. A thickened suspension is then recirculated to the suction side of the first centrifugal pump. The hydrogenation product is typically freed of suspended solid by filtration and afterwards distilled. As discussed in example 3, an amount of hydrogenation product is taken off continuously via an overflow and introduced into a decanting vessel. From this intermediate vessel, the product is continuously fed to the work-up by distillation.

The work-up by distillation can be performed as described in SRI report 1a, 1968, pages 55 to 65 or as disclosed in US 2007/0083065, for example.

Typically, the low-boiling constituents of the hydrogenation product are removed overhead. The bottoms mixture is fed to a thin-film evaporator in which the toluylene isomer mixture is removed.

As an alternative, a second rectification column can be employed, wherein the TDA isomer mixture is drawn off over-head. The remaining bottoms which comprise in particular the oligomer mixture form from the TDA isomers and the catalyst from the hydrogenation are then obtained as the TDA tar.

These high boilers forming the TDA tar are composed substantially of oligomers and polymers which are formed by reaction of the TDA isomers with each other. The oligomers and polymers are substantially secondary or tertiary amines. The oligomers and polymers are substantially azo, azoxy or hydrazine compounds, cf. paragraph [0016] of US 2007/0083065.

Thus, the toluenediamine (TDA) tar employed according to the present invention can be defined as the bottom residue of a two-step distillation of TDA derived from dinitrotoluene in which first low-boiling constituents are removed overhead and then in the second rectification column TDA isomer mixtures are drawn off overhead.

The bottoms, however, additionally contain significant residual amounts of TDA isomers, e.g. 5 to 35 wt %, in order to keep the bottoms flowable and to reduce their viscosity. Thus, the TDA tar contains TDA and high boilers relative to TDA.

Upon hydrogenation or hydrogenating conditions, part of the high boilers is preferably transformed into mid-boilers or low boilers having a lower boiling point than the high boilers.

The terms high boilers (HB), mid-boilers (MB) and low boilers (LB) have no clear-cut edges to the boiling temperature range. However, low boilers have a boiling point lower than TDA, whereas mid-boilers have a boiling temperature higher than TDA and high boilers have a boiling point even higher than the mid-boilers. Mid-boilers are typically ring-hydrogenated dimers, whereas high boilers are the non-hydrogenated dimers. High boilers relative to TDA are those compounds having a higher boiling point than TDA.

MCA is a typical part of low boilers. 1,4-dioxane, a suitable solvent, has an even lower boiling point.

In a preferred embodiment of the present invention, the toluenediamine (TDA) tar containing TDA and high boilers relative to TDA are converted into methylcyclohexylamine (MCA) and/or methylcyclohexyldiamine (MCDA). The latter compounds are valuable intermediate products for the manufacture of chemicals.

A yield from the TDA tar as high as 47% with regard to MC(D)A could be obtained by the process of the present invention.

The isomer distribution of MCDA depends on the isomer distribution in the TDA. Vicinal TDA results in a corresponding enrichment of vicinal MCDA.

The process according to the present invention allows the hydrogenation of the aromatic core of the TDA on the one hand. On the other hand, it also allows to reduce the size of the high-boiling polyamines via hydrogenolysis. In this way, the highly viscous high boilers can be transformed into medium boilers or low boilers which can replace the TDA in providing the necessary flow behavior to the TDA tar.

Therefore, TDA can be removed from the TDA tar after the hydrogenolysis without impairing the flow behavior.

A GC analysis of the feed solution for the process of the present invention, for example, leads to 70% of the area % of high boilers, 25% of TDA, the remainder being mid-boilers.

The feed and product can be analysed by GC employing a column RTX-5 amine, 30 m, 0.32 mm, 1.5 μm starting with 125° C. for 1 min and then heating up to 285° C. with 5 K/min. Low boilers are all components with a retention time smaller than TDA. Mid-boilers have higher retention times. The split between mid- and high boilers was set to 36 min (shortly after the final column temperature is achieved).

The GC shows in this sequence 1,4-dioxane, MCA, low boilers, TDA, mid-boilers (ring-hydrogenated dimers) and high boilers (dimers).

In the examples, product compositions are given that are calculated by the relative share of the component group normalized to the Area % of all products and educts, i.e. leaving out the solvent Area % (content product×Area % (X)/Σ Area % (non-solvents)). Conversion of TDA and high boilers is calculated with reference to the feed content of these (X (TDA)=1−content (TDA in product)/content (TDA in feed)). The overall content of high boilers by this method is reduced due to the lower sensitivity of the GC towards these. Correspondingly, the TDA content of the feed may be overestimated.

According to the present invention, it has been found that specific catalysts catalyze the hydrogenation of TDA tar. Whereas copper-containing catalysts and rhodium-containing catalysts have been found to be inactive, suitable catalysts comprise at least one metal selected from the group consisting of Ni, Co, Ru, Pd, Pt on at least one catalyst support selected from the group consisting of carbon, $TiO_2$ and $ZrO_2$.

Preferably, the catalyst comprises Ni, Ni and Pt, Ru, Pd, or Pt as hydrogenating metal(s) on a $ZrO_2$ or active carbon catalyst support.

Preferably, the amount of Ru, Pd, Pt or mixtures thereof, based on the heterogeneous hydrogenation catalyst, is 1 to 7 wt %, preferably 3 to 5 wt %.

Preferably, the amount of Ni, Co or mixtures thereof, based on the heterogeneous hydrogenation catalyst, is 0.5 to 70 wt %, more preferably 1 to 60 wt %. If Ni and/or Co are employed without a noble metal, the amount is more preferably 50 to 70 wt %, most preferably 55 to 65 wt %.

If, however, a noble metal is the base metal and Ni and/or Co are employed as a further metal, their amount is in the range of from 0.5 to 2 wt %, more preferably 0.8 to 1.5 wt %. Most preferably the heterogeneous hydrogenation catalyst is Ni/$ZrO_2$, Ru/$ZrO_2$, Pd/C, Pt/C or Pt/Ni/C.

Most preferably, ruthenium-zirconia catalysts are employed.

This catalyst can be as described in WO 2015/086638.

Appropriate catalysts may be prepared by known processes such as impregnation, described, for example, in A. B. Stiles, Catalyst Manufacture—Laboratory and Commercial Preparations, Marcel Dekker, New York, 1983, or precipitation, described, for example, in EP 1 106 600, page 4, and A. B. Stiles, Catalyst Manufacture, Marcel Dekker, Inc., 1983, page 15.

The catalysts to be used according to the invention can be prepared by applying useful ruthenium compounds, for example ruthenium salts, to extrudates, pellets or spheres of the zirconium oxide support material having diameters, for example, from about 1.5 to 10 mm. Subsequently, the catalyst is generally dried at a temperature of from 80 to 180° C., for example 120° C., and calcined at a temperature of from 180 to 450° C., for example 180° C.; both steps may also be effected simultaneously. Ruthenium salts useful for application include, for example, those selected from the group consisting of ruthenium acetate, acetylacetonate, chloride, nitrosyl nitrate and mixtures thereof.

An accordingly prepared catalyst is generally ready for use according to the invention following the drying step. It is, however, preferable to activate the catalyst by treatment with hydrogen at a temperature of, for example, 150 to 400° C. before use, and it is more preferable to do so after the catalyst has been placed in the reactor provided for the hydrogenation according to the invention.

It is preferable according to the invention for the support material zirconium oxide ($ZrO_2$) to be present in monoclinic, tetragonal, cubic or amorphous phase, or in a mixed phase, monoclinic or tetragonal phase or a mixed phase of these forms being particularly preferable.

It is therefore preferable for the present invention to relate to the process according to the invention, wherein the zirconium oxide support material is present in monoclinic, tetragonal, cubic or amorphous phase, or in a mixed phase of these modifications.

The present invention further preferably relates to the process according to the invention, wherein the zirconium oxide support material is present in monoclinic, tetragonal, cubic or amorphous phase, or in a mixed phase of these modifications.

It is preferable according to the invention, for the zirconium oxide support material, preferably prior to applying ruthenium, to have a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption according to DIN 66131.

It is preferable according to the invention, for the zirconium oxide support material, preferably prior to applying ruthenium, to have a pore volume of from 0.1 to 1 $cm^3/g$, preferably 0.1 to 0.9 $cm^3/g$, in each case determined by mercury porosimetry according to DIN 66133.

It is preferable according to the invention, for the zirconium oxide support material of the inventive catalyst used in suspension, preferably prior to applying ruthenium, to have a pore volume of from 0.1 to 1 $cm^3/g$, preferably 0.5 to 1 $cm^3/g$, more preferably 0.7 to 0.9 $cm^3/g$, in each case determined by mercury porosimetry according to DIN 66133.

It is preferable according to the invention, for the zirconium oxide support material of the invention catalyst used in a fixed bed, preferably prior to applying ruthenium, to have a pore volume of from 0.1 to 1 $cm^3/g$, preferably 0.1 to 0.6 $cm^3/g$, more preferably 0.1 to 0.5 $cm^3/g$, in each case determined by mercury porosimetry according to DIN 66133.

It is preferable according to the invention, for the zirconium oxide support material, preferably prior to applying the ruthenium, to have a tamped density of from 500 to 2000 $kg/m^3$, preferably 600 to 1800 $kg/m^3$, more preferably 700 to 1750 $kg/m^3$, in each case determined in a STAV2003 tamping volumeter from JEL, the sample having been tamped 2000 times.

It is particularly preferable according to the invention, for the zirconium oxide support material, preferably prior to applying the ruthenium, to have a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption, a pore volume of from 0.1 to 1 $cm^3/g$, preferably 0.1 to 0.8 $cm^3/g$, more preferably 0.1 to 0.7 $cm^3/g$, in each case determined by mercury porosimetry, and a tamped density of from 500 to 2000 $kg/m^3$, preferably 600 to 1750 $kg/m^3$, more preferably 700 to 1500 $kg/m^3$, in each case determined in a STAV2003 tamping volumeter from JEL, the sample having been tamped 2000 times.

The present invention therefore preferably relates to the process according to the invention, wherein the zirconium oxide support material, preferably prior to applying the ruthenium, has a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption, a pore volume of from 0.1 to 1 cm$^3$/g, preferably 0.1 to 0.8 cm$^3$/g, more preferably 0.1 to 0.7 cm$^3$/g, in each case determined by mercury porosimetry, and a tamped density of from 500 to 2000 kg/m$^3$, preferably 600 to 1800 kg/m$^3$, more preferably 700 to 1500 kg/m$^3$, in each case determined in a STAV2003 tamping volumeter from JEL, the sample having been tamped 2000 times.

It is particularly preferable according to the invention for the zirconium oxide support material, preferably prior to applying the ruthenium, to have a monoclinic or tetragonal modification (or a mixture of both of these), a BET surface area of from 30 to 300 m$^2$/g, preferably 35 to 250 m$^2$/g, more preferably 50 to 90 m$^2$/g or more than 90 to 100 m$^2$/g, i.e., 50 to 100 m$^2$/g, in each case determined by nitrogen sorption, a pore volume of from 0.1 to 1 cm$^3$/g, preferably 0.1 to 0.8 cm$^3$/g, more preferably 0.1 to 0.7 cm$^3$/g, in each case determined by mercury porosimetry, and a tamped density of from 500 to 2000 kg/m$^3$, preferably 600 to 1800 kg/m$^3$, more preferably 700 to 1500 kg/m$^3$, in each case determined in a STAV2003 tamping volumeter from JEL, the sample having been tamped 2000 times.

The present invention therefore preferably relates to the process according to the invention, wherein the zirconium oxide support material, preferably prior to applying the ruthenium, has a monoclinic or tetragonal modification (or a mixture of both of these), a BET surface area of from 30 to 300 m$^2$/g, preferably 35 to 250 m$^2$/g, more preferably 50 to 90 m$^2$/g or more than 90 to 100 m$^2$/g, i.e., 50 to 100 m$^2$/g, in each case determined by nitrogen sorption, a pore volume of from 0.1 to 1 cm$^3$/g, preferably 0.1 to 0.8 cm$^3$/g, more preferably 0.1 to 0.7 cm$^3$/g, in each case determined by mercury porosimetry, and a tamped density of from 500 to 2000 kg/m$^3$, preferably 600 to 1800 kg/m$^3$, more preferably 700 to 1500 kg/m$^3$, in each case determined in a STAV2003 tamping volumeter from JEL, the sample having been tamped 2000 times. It is preferable according to the invention for the zirconium oxide support material of the catalyst used in the fixed bed to have a pore size distribution where more than 50% of the pores present are formed by mesopores having a diameter of from 2 nm to 50 nm and the remainder to 100% are formed by macropores having a diameter of >50 nm.

The present invention therefore preferably relates to the process according to the invention, wherein the zirconium oxide support material of the catalyst used in the fixed bed has a pore size distribution where more than 50% of the pores present are formed by mesopores having a diameter of from 2 nm to 50 nm and the remainder to 100% are formed by macropores having a diameter of >50 nm.

It is preferable according to the invention for the zirconium oxide support material of the catalyst used in suspension to have a pore size distribution where more than 40% of the pores present are macropores having a diameter of >50 nm and the remainder to 100% are formed by mesopores having a diameter of from 2 nm to 50 nm.

The present invention therefore preferably relates to the process according to the invention, wherein the zirconium oxide support material of the catalyst used in suspension has a pore size distribution where more than 40% of the pores present are macropores having a diameter of >50 nm and the remainder to 100% are formed by mesopores having a diameter of from 2 nm to 50 nm.

The present invention preferably relates to the process according to the invention, wherein the catalyst has a BET surface area of from 30 to 300 m$^2$/g, preferably 50 to 90 m$^2$/g or more than 90 to 100 m$^2$/g, i.e., 50 to 100 m$^2$/g, a pore volume of from 0.1 to 1 cm$^3$/g, preferably 0.1 to 0.9 cm$^3$/g, and a tamped density of from 500 to 2000 kg/m$^3$, preferably 700 to 1750 kg/m$^3$.

The present invention preferably also relates to the process according to the invention, wherein the catalyst used in the fixed bed has a pore size distribution where more than 50% of the pores present are formed by mesopores having a diameter of from 2 nm to 50 nm and the remainder to 100% are formed by macropores having a diameter of >50 nm.

The present invention preferably also relates to the process according to the invention, wherein the catalyst used in suspension has a pore size distribution where more than 40% of the pores present are formed by macropores having a diameter of >50 nm and the remainder to 100% are formed by mesopores having a diameter of from 2 nm to 50 nm.

The process according to the present invention can be carried out in suspension or in a fixed bed. It can be furthermore carried out as a continuous operation or batchwise.

The process according to the present invention is preferably carried out at a temperature of from 120 to 270° C., preferably 150 to 250° C.

The process is preferably carried out at a hydrogen pressure of from 60 to 300 bar, more preferably from 100 to 200 bar.

The TDA tar can be employed as such. It is furthermore possible to employ the TDA tar as a, e.g. 5 to 90 wt %, solution in a solvent or diluent. Typically, organic solvents or diluents are employed. One specifically preferred example is 1,4-dioxane.

The present invention is further illustrated by the following examples.

Percentages are wt %, based on the respective catalyst.

EXAMPLES

General Procedure:

All experiments were performed in a lab autoclave in batch mode. The 100 ml autoclave was filled with catalyst (typically 2 g) and 50 g 7 wt % solution of TDA tar in 1,4-dioxane. After this it was pressurized with nitrogen for leak-test and depressurized. To purge out nitrogen a pressurization with hydrogen followed with depressurization was applied. Then the autoclave was heated to reaction temperature (typically 170° C.) stirring with 1000 rpm. At reaction temperature the system was pressurized with hydrogen to the reaction pressure (typically 150 bar) which is regarded as the starting time. Liquid is sampled manually typically after 3, 5 and 24 h after pressurization with hydrogen and the samples are analyzed by GC.

Example 1

Apart from 3% Pt-1% Ni/C (1 g) always 2 g of catalysts were employed. To enable handling of the Rh-carbon catalyst which is pyrophoric the catalyst was pre-immersed in 10 g diethyleneglycol and 40 g of the tar-solution was employed to avoid overfilling of the autoclave.

Results after 3 h are given in Table 1. Summarizing the catalyst testing program it can be stated:

Base Metal Catalysts

| Ni catalysts (60% Ni/ZrO$_2$) | moderately active |
| Cu catalysts | inactive |

Precious Metal Catalysts

| 5% Ru/ZrO$_2$ (BASF) | moderately active/MCDA as product |
| 3% Pd/C (Aldrich) & (BASF 5% Pd/C) | very active/MCA as product |
| 3% Rh/C (Aldrich) | inactive |
| 3% Pt/C (Aldrich) & (3% Pt-1% Ni/C) | moderately active but only to mid-boilers |

Example 2

Ni Catalyst:

Test results for a nickel-zirconia catalyst are given in Table 2. After 3 h the temperature was elevated to 190° C. resulting in strong increase in MCA yield. After 24 h more than 70% of the high boilers are converted and TDA is only partially converted. The main fraction is composed of the mid-boilers (35% yield) but MCA yield is considerably high with 24%.

TABLE 1

Conversion of high boilers resp. TDA and corresponding product composition after 3 h

| | | | relative product composition | | | | | | |
|---|---|---|---|---|---|---|---|---|---|
| | X(HB) [%] | X(TDA) [%] | HB [%] | TDA [%] | MCDA [%] | MCA [%] | Toluidine [%] | other LB [%] | MB [%] |
| 60% Ni/ZrO$_2$ 3 h@170° C. | 22% | 18% | 50% | 26% | 1% | 2% | 0% | 12% | 9% |
| Cu—Zn—AlO$_3$ 3 h@170° C. | 6% | −4% | 66% | 26% | 0% | 3% | 0% | 1% | 4% |
| Cu—Mn/Al$_2$O$_3$ 3 h@170° C. | 7% | −10% | 65% | 28% | 0% | 0% | 0% | 1% | 5% |
| 5% Ru/ZrO$_2$ 3 h@170° C. | 15% | 51% | 59% | 12% | 14% | 4% | 0% | 1% | 8% |
| 5% Pd/C 3 h@170° C. | 57% | 65% | 30% | 9% | 1% | 15% | 4% | 14% | 26% |
| 3% Pd/C 3 h@170° C. | 49% | 63% | 36% | 10% | 2% | 11% | 4% | 10% | 27% |
| 3% Rh/C 3 h@170° C. | −2% | 63% | 61% | 10% | 3% | 2% | 1% | 7% | 11% |
| 3% Pt/C 3 h@170° C. | 14% | −9% | 60% | 28% | 0% | 0% | 0% | 1% | 8% |
| 3% Pt—1% Ni/C 3 h@170° C. | 10% | −6% | 57% | 33% | 0% | 0% | 0% | 1% | 8% |

TABLE 2

| | X(HB) [%] | X(TDA) [%] | HB [%] | TDA [%] | MCDA [%] | MCA [%] | Toluidine [%] | other LB [%] | MB [%] |
|---|---|---|---|---|---|---|---|---|---|
| | | | | | relative product composition | | | | |
| 60% Ni/ZrO$_2$ 3 h@170° C. | 22% | 18% | 50% | 26% | 1% | 2% | 0% | 12% | 9% |
| 60% Ni/ZrO$_2$ + 2 h@190° C. | 31% | 28% | 44% | 23% | 2% | 6% | 0% | 11% | 15% |
| 60% Ni/ZrO$_2$ + 19 h@190° C. | 72% | 52% | 18% | 15% | 2% | 24% | 1% | 6% | 35% |

Example 3

Pd Catalyst:

Test results for catalyst (5% Pd/carbon) are given in Table 3. After 24 h almost 90% of the high boilers are converted and TDA is fully converted. The main fraction is composed of the mid-boilers (46% yield).

The MCA-yield is considerably high with 23%. The distribution between 2-methylcyclohexylamine and 4-methylcyclohexylamine is around 1:1. The relative share of cis/trans-isomers of the two regio-isomers lies between 1:1 and 1:3 however the assignment to cis or trans is not established. Furthermore the base-line separation of the first peaks of both region-isomers i.e. 2MCA_a and 4MCA_a is not given so that the twin-peak was arbitrarily split at the minimum.

TABLE 3

Conversion of high boilers resp. TDA and corresponding product composition after 3, 5 and 24 h

| | X(HB) [%] | X(TDA) [%] | HB [%] | TDA [%] | MCDA [%] | MCA [%] | Toluidine [%] | other LB [%] | MB [%] |
|---|---|---|---|---|---|---|---|---|---|
| | | | | | relative product composition | | | | |
| 5% PdC 3 h@170° C. | 57% | 65% | 30% | 9% | 1% | 15% | 4% | 14% | 26% |
| 5% PdC + 2 h@170° C. | 76% | 92% | 17% | 2% | 2% | 22% | 5% | 16% | 37% |
| 5% PdC + 19 h@170° C. | 89% | 99% | 8% | 0% | 3% | 23% | 5% | 16% | 46% |

Example 4

Ru Catalyst:

Test results for 5% Ru/ZrO$_2$ are given in Table 4. After 24 h at 190° C. almost 70% of the high boilers are converted and TDA is fully converted. The main product fractions are MCA-isomers, MCDA-isomers and mid-boilers. To known value products MCA and MCDA the yield is 47%. At 170° C. the conversion of high boilers is considerably low and mostly TDA is converted to MCDA.

TABLE 4

Conversion of high boilers resp. TDA and corresponding product composition at various times for two temperatures

| | X(HB) [%] | X(TDA) [%] | HB [%] | TDA [%] | MCDA [%] | MCA [%] | Toluidine [%] | other LB [%] | MB [%] |
|---|---|---|---|---|---|---|---|---|---|
| | | | | | relative product composition | | | | |
| 5% Ru/ZrO$_2$ 3 h@170° C. | 15% | 51% | 59% | 12% | 14% | 4% | 0% | 1% | 8% |
| 5% Ru/ZrO$_2$ + 2 h@170° C. | 18% | 65% | 58% | 9% | 17% | 5% | 0% | 2% | 9% |
| 5% Ru/ZrO$_2$ 3 h@190° C. | 27% | 77% | 51% | 6% | 20% | 9% | 1% | 3% | 10% |
| 5% Ru/ZrO$_2$ + 2 h@190° C. | 32% | 81% | 48% | 5% | 21% | 10% | 0% | 4% | 12% |

TABLE 4-continued

Conversion of high boilers resp. TDA and corresponding product composition at various times for two temperatures

| | | | | | | | relative product composition | | |
|---|---|---|---|---|---|---|---|---|---|
| | X(HB) [%] | X(TDA) [%] | HB [%] | TDA [%] | MCDA [%] | MCA [%] | Toluidine [%] | other LB [%] | MB [%] |
| 5% Ru/ZrO$_2$ + 19 h@190° C. | 69% | 95% | 22% | 1% | 26% | 21% | 0% | 8% | 21% |

The invention claimed is:

1. A process for hydrogenating a toluenediamine (TDA) tar containing TDA and high boilers relative to TDA, the process comprising:

contacting the toluenediamine tar with a heterogeneous hydrogenation catalyst comprising at least one metal selected from the group consisting of Ni, Co, Ru, Pd, Pt on at least one catalyst support selected from the group consisting of carbon, TiO$_2$ and ZrO$_2$, and with hydrogen under hydrogenating conditions, wherein the toluenediamine tar contains 5 to 35 wt % of toluenediamine isomers.

2. The process according to claim 1, wherein the catalyst comprises Ni, Ni and Pt, Ru, Pd, or Pt on a ZrO$_2$ or an active carbon catalyst support.

3. The process according to claim 1, wherein an amount of Ru, Pd, Pt or mixtures thereof, based on the heterogeneous hydrogenation catalyst, is 1 to 7 wt %.

4. The process according to claim 1, wherein an amount of Ni, Co or mixture thereof, based on the heterogeneous hydrogenation catalyst, is 0.5 to 70 wt %.

5. The process according to claim 1, wherein the heterogeneous hydrogenation catalyst is Ni/ZrO$_2$, Ru/ZrO$_2$, Pd/C, Pt/C or Pt/Ni/C.

6. The process according to claim 1, which is carried out in suspension or in a fixed bed.

7. The process according to claim 1, which is carried out as a continuous operation or batchwise.

8. The process according to claim 1, which is carried out at a temperature of from 120 to 270° C.

9. The process according to claim 1, which is carried out at a hydrogen pressure of from 60 to 300 bar.

10. The process according to claim 1, wherein the zirconium oxide support material is present in monoclinic, tetragonal, cubic or amorphous phase or in a mixed phase of these modifications.

11. The process according to claim 1, wherein the zirconium oxide support material has a BET surface area of from 30 to 300 m$^2$/g a pore volume of from 0.1 to 1 cm$^3$/g and a tamped density of from 500 to 2000 kg/m$^3$.

12. The process according to claim 1, wherein upon hydrogenation, part of the high boilers are transformed into mid-boilers or low boilers having a lower boiling point than the high boilers.

13. The process according to claim 1, wherein part of the toluenediamine (TDA) tar containing TDA and high boilers relative to TDA are converted into methylcyclohexylamine (MCA) and/or methylcyclohexyldiamine (MCDA).

14. The process according to claim 1, wherein the toluenediamine tar is diluted with an organic solvent or diluent inert to the hydrogenation before performing the hydrogenation.

* * * * *

UNITED STATES PATENT AND TRADEMARK OFFICE
CERTIFICATE OF CORRECTION

PATENT NO. : 10,662,141 B2
APPLICATION NO. : 16/340478
DATED : May 26, 2020
INVENTOR(S) : Armin Lange De Oliveira et al.

It is certified that error appears in the above-identified patent and that said Letters Patent is hereby corrected as shown below:

In the Specification

Column 3, Line 7, "toluene diamine" should read -- toluenediamine --

Column 3, Line 26, "dinitrotolulene" should read -- dinitrotoluene --

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*